United States Patent [19]

Gabriel et al.

[11] Patent Number: 5,824,097
[45] Date of Patent: Oct. 20, 1998

[54] MEDICAL FASTENING SYSTEM

[75] Inventors: Stefan M. Gabriel, Lakeville; Dennis P. Colleran, Plainville, both of Mass.

[73] Assignee: Johnson & Johnson Professional, Inc., Raynham, Mass.

[21] Appl. No.: 696,495

[22] Filed: Aug. 14, 1996

Related U.S. Application Data

[63] Continuation-in-part of Ser. No. 685,289, Jul. 23, 1996.
[51] Int. Cl.⁶ ....................................................... A61F 2/38
[52] U.S. Cl. .............................................................. 623/20
[58] Field of Search ................................. 623/18, 19, 20, 623/23; 606/69, 73

[56] References Cited

U.S. PATENT DOCUMENTS

| | | | |
|---|---|---|---|
| 4,219,893 | 9/1980 | Noiles | 3/1.911 |
| 4,301,553 | 11/1981 | Noiles | 3/1.911 |
| 4,624,673 | 11/1986 | Meyer | 623/16 |
| 4,790,852 | 12/1988 | Noiles | 623/18 |
| 4,822,366 | 4/1989 | Bolesky | 623/20 |
| 4,846,839 | 7/1989 | Noiles | 623/18 |
| 4,888,021 | 12/1989 | Forte et al. | 623/20 |
| 4,904,110 | 2/1990 | Klein | 403/379 |
| 4,985,037 | 1/1991 | Petersen | 628/20 |
| 5,011,496 | 4/1991 | Forte et al. | 623/20 |
| 5,057,111 | 10/1991 | Park | 606/69 |
| 5,127,914 | 7/1992 | Calderale et al. | 606/65 |
| 5,133,760 | 7/1992 | Peterson et al. | 623/20 |
| 5,152,796 | 10/1992 | Slamin | 623/20 |
| 5,269,784 | 12/1993 | Mast | 606/69 |
| 5,290,313 | 3/1994 | Heldreth | 623/20 |
| 5,326,359 | 7/1994 | Oudard | 623/20 |
| 5,336,225 | 8/1994 | Zang | 606/73 |
| 5,405,395 | 4/1995 | Coates | 623/20 |

FOREIGN PATENT DOCUMENTS

| | | | |
|---|---|---|---|
| 0529408 | 3/1993 | European Pat. Off. | 623/20 |
| 05311263 | 3/1993 | European Pat. Off. | |
| 0473375 | 3/1929 | Germany | 411/398 |

OTHER PUBLICATIONS

Johnson & Johnson Orthopaedics Research & Development "P.F.C.®*Modular Knee System Research Data and Laboratory Testing*", cover and pp. 8, 36 and 37 (1989).

*Primary Examiner*—David Isabella
*Attorney, Agent, or Firm*—Nutter, McClennen & Fish, LLP

[57] ABSTRACT

A medical fastening system for a modular knee prosthesis includes a femoral component having an aperture. A washer having an aperture alignable with at least a portion of the aperture in the femoral component engages the femoral component to inhibit movement of the washer through the aperture in the femoral component. A bolt engages the washer and an elongate shaft portion of the bolt protrudes from the femoral component through the aperture in the washer and the aperture in the femoral component to engage a Morse taper post or femoral stem. The configuration of the washer aperture, its location in the washer, and the orientation of the washer within the femoral component determine the fore and aft positioning of the Morse taper post or femoral stem. The Morse taper post or femoral stem can be provided with a canted base to angle the post or stem with respect to the femoral component.

6 Claims, 8 Drawing Sheets

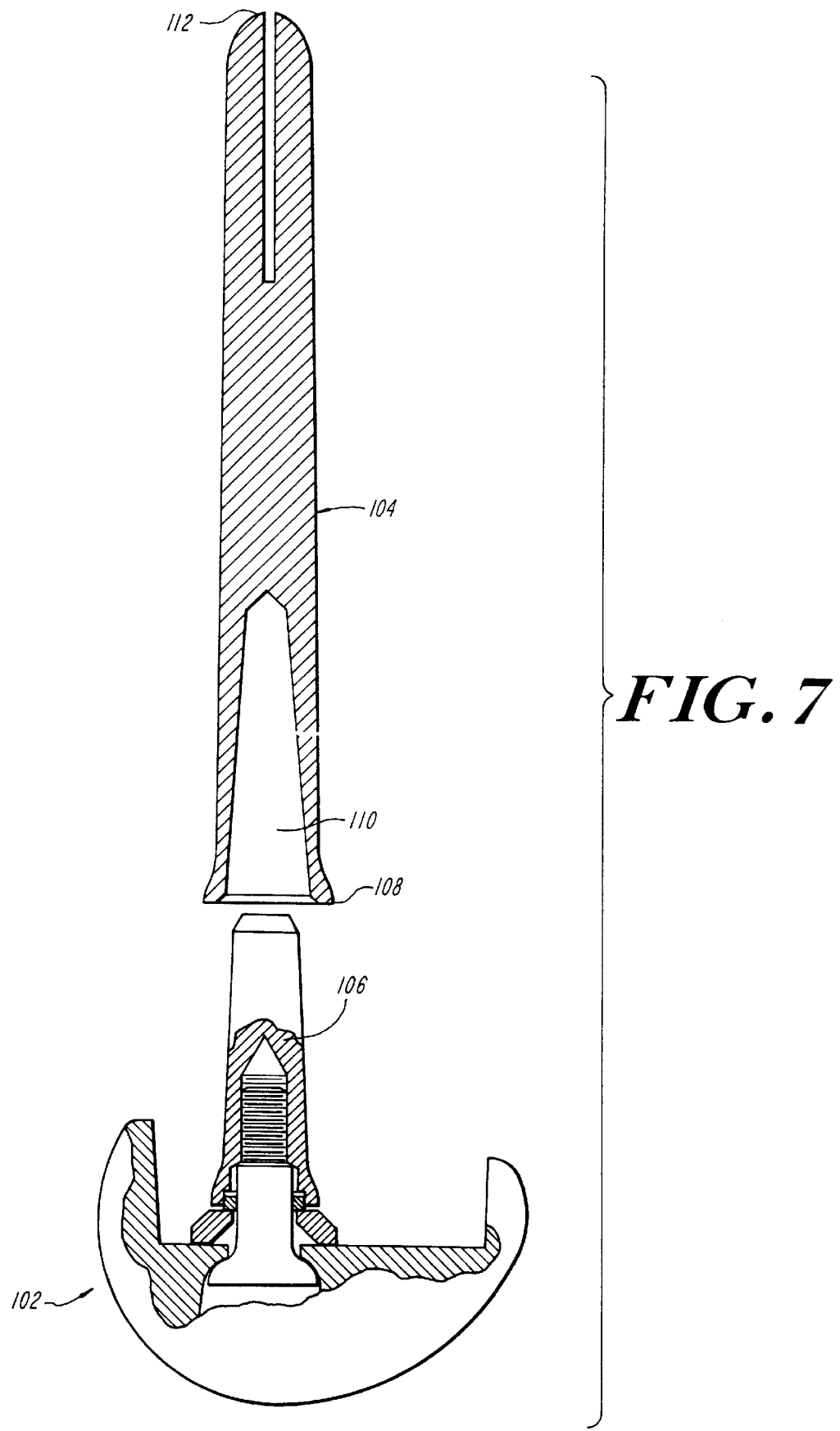

MEDICAL FASTENING SYSTEM

CROSS-REFERENCE TO RELATED APPLICATIONS

The present application is a continuation-in-part of a commonly assigned patent application Ser. No. 08/685,289 filed Jul. 23, 1996, pending, entitled MODULAR KNEE PROSTHESIS.

FIELD OF THE INVENTION

This invention relates to joint prostheses, and more particularly to modular knee joint prostheses employed during knee arthroplasty procedures.

BACKGROUND OF THE INVENTION

Knee arthroplasty is a well-known surgical procedure by which a diseased and/or damaged natural knee joint is replaced by a prosthetic knee joint. Typical knee prostheses include a tibial component, a femoral component, and a patellar component. The femoral component generally includes a pair of spaced apart condylar portions, the superior surfaces of which articulate with a portion of the tibial component. A femoral stem assembly, used to provide lateral stability to the replaced knee joint, seats within the medullary canal of a distal portion of a femur, and is typically coupled to the femoral component by specialized coupling devices, such as a collar and bolt. Some prosthetic knee joints include a structure known as a Morse taper post that extends from the inferior surface of the femoral component to mate with a femoral sleeve that is securable to the femoral stem assembly.

The femoral sleeve, which helps to fill spaces at the opening of the medullary canal, can also provide for a modular assembly allowing a surgeon to select the most appropriate femoral stem from a selection of stems having different lengths and diameters for attachment to one of a selection of femoral components. This modular configuration significantly reduces the number of individual components that must be purchased, stocked, and used during a surgical procedure. Although the femoral stem, whatever its dimensions, is usually angled laterally with respect to the inferior surface of the femoral component and either off-set anteriorially/posterially or at a central location, it is sometimes desirable to orient the femoral stem perpendicularly with respect to the inferior surface. For example, depending on particular patient requirements, the femoral stem may need to be offset fore or aft with respect to the front of the femoral component. Similarly, the femoral stem may need to be angled varying degrees to the left or right with respect to the front of the femoral component. The Morse taper post, however, is integrally cast as a unitary and indivisible portion of the femoral component. Furthermore, there is a requirement for a range of sizes of the overall femoral component. Therefore, in order to accommodate all of the possible combinations of overall femoral component size, fore/neutral/aft positioning of the Morse taper post, and left/perpendicular/right angling of the Morse taper post, a doctor or hospital is required to maintain an undesirably substantial stock of knee prosthesis components.

Despite the existence of knee joint prostheses having modular components, there remains a need for a modular knee joint prosthesis that has greater versatility to accommodate differing patient anatomy and joint conditions. It is thus an object of the invention to provide a modular knee prosthesis having greater versatility to accommodate different patient anatomy and joint conditions while maintaining a relatively low component count. It is another object of the invention to provide a modular knee prosthesis having components that are physiologically and geometrically compatible with different anatomical conditions. Still another object of the invention is to provide a modular knee prosthesis that is suitable for use in both right and left knee procedures. Other general and more specific objects of the invention will in part be apparent from the drawings and description that follow.

SUMMARY OF THE INVENTION

The present invention relates to a modular knee joint prosthesis having improved versatility while reducing the overall component count. Components of the modular prosthesis of the invention are able to be used with both right and left side prostheses.

In an exemplary embodiment of the invention, a modular knee prosthesis includes a femoral component, a bolt, and a Morse taper post. The femoral component has a superior surface, an inferior surface, and an aperture extending therebetween. The bolt includes a head portion engagable with the superior surface of the femoral component to inhibit movement of the bolt through the femoral component, and an elongate shaft portion that extends from the head portion of the bolt. The elongate shaft portion has a length sufficient to protrude through the aperture beyond the inferior surface of the femoral component. The Morse taper post is engagable with the elongate shaft portion of the bolt to retain the Morse taper post in a fixed position with respect to the femoral component and the distal end of the Morse taper post is introducible within a femoral sleeve.

The modular knee prosthesis can further include a collar interposable between the Morse taper post and the inferior surface of the femoral component. The collar can position the elongate shaft portion of the bolt or the Morse taper post orthogonally or at an angle, in the medial or lateral directions, with respect to the inferior surface of the femoral component.

Additionally, the aperture of the femoral component can be configured to allow the shaft portion of the bolt to be extended through the aperture at a predetermined angle with respect to the inferior surface of the femoral component and be held at the predetermined angle by a collar. The aperture and the bolt are cooperatively configured to position the Morse taper post fore and aft with respect to a central reference location.

In another embodiment of the invention, a modular knee fastening system for a modular knee prosthesis includes a washer engagable with a bolt and a femoral component so that a portion of the bolt shaft protrudes through an aperture in the washer and an aperture in the femoral component. The washer can include an aperture that is in the center of the washer, off-center, or lobed to permit selective placement of the bolt with respect to the femoral component In yet another embodiment of the invention, a medical fastening system for a modular knee prosthesis includes a femoral component having an aperture. A washer having an aperture alignable with at least a portion of the aperture in the femoral component engages the femoral component to inhibit movement of the washer through the aperture in the femoral component. A bolt engages the washer and an elongate shaft portion of the bolt protrudes from the femoral component through the aperture in the washer and the aperture in the femoral component to engage a Morse taper post or femoral stem. The configuration of the washer aperture, its location in the washer, and the orientation of the washer within the femoral component determine the fore and aft positioning of the Morse taper post or femoral stem. The Morse taper post or femoral stem can be provided with a canted base to angle the post or stem with respect to the femoral component.

BRIEF DESCRIPTION OF THE DRAWINGS

The foregoing and other objects, features and advantages of the invention will be apparent from the following description and the accompanying drawings, in which like reference characters refer to the same parts throughout the different views.

FIG. 7 is a cutaway exploded view of an a modular knee prosthesis according to the present invention, wherein a femoral stem is directly mountable on a Morse taper post;

DETAILED DESCRIPTION OF THE INVENTION

Figure 1:
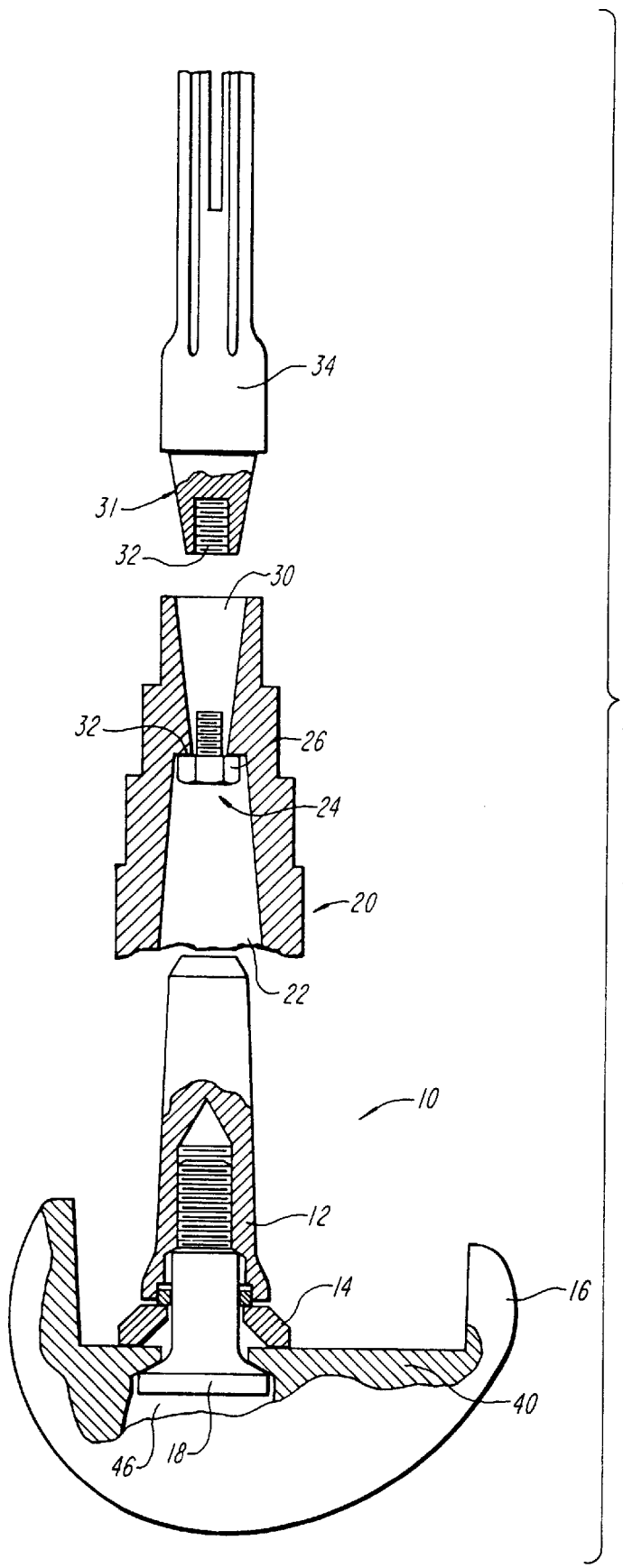
FIG. 1 is a cutaway exploded view of a modular knee prosthesis according to the present invention that includes a right knee femoral component.

As illustrated in FIG. 1, a modular knee prosthesis 10 of the invention includes a Morse taper post 12, a collar 14, a femoral component 16, and a securing bolt 18. Although the illustrated modular knee prosthesis 10 includes a femoral component 16 adapted for a right knee, the Morse taper post 12, collar 14, and securing bolt 18 are suitable for use, without modification, in association with a femoral component adapted for a left knee.

A femoral sleeve 20, adapted for mating with the Morse taper post 12, includes a first end that defines a first cavity 22 for receiving the distal end portion of the Morse taper post. In the illustration, the first cavity 22 is tapered to provide a friction fit over the Morse taper post 12. A femoral sleeve stem bolt 24, having a head 26 and a shank 28 is positionable within the femoral sleeve 20. The shank 28 projects into a second cavity 30 defined in the second end of the femoral sleeve 20. In an exemplary embodiment, the femoral sleeve 20 includes a constriction or shoulder 32 that prevents the head 26 from entering into the second cavity 30 or otherwise anchors the femoral sleeve stem bolt 24 within the femoral sleeve 20. The femoral sleeve stem bolt 24 is adapted to engage a mating portion 32 of a femoral stem 34 selected from a group of femoral stems having different lengths and diameters. The illustrated femoral stem has a tapered end 31 that is receivable within the second cavity 30 of the femoral sleeve, which has a complimentary taper. In other embodiments of the invention, the Morse taper post is directly matable with a femoral stem or other component without a femoral sleeve.

Figure 2:
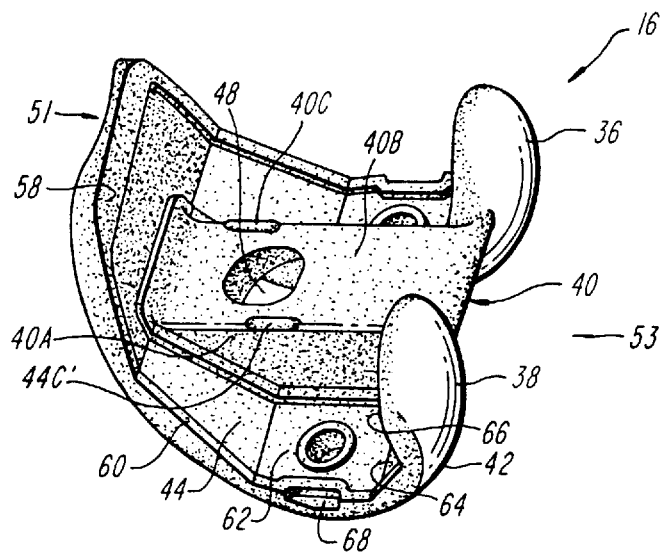
FIG. 2 is a perspective view of the femoral component of the modular knee prosthesis of FIG. 1.
Figure 3:
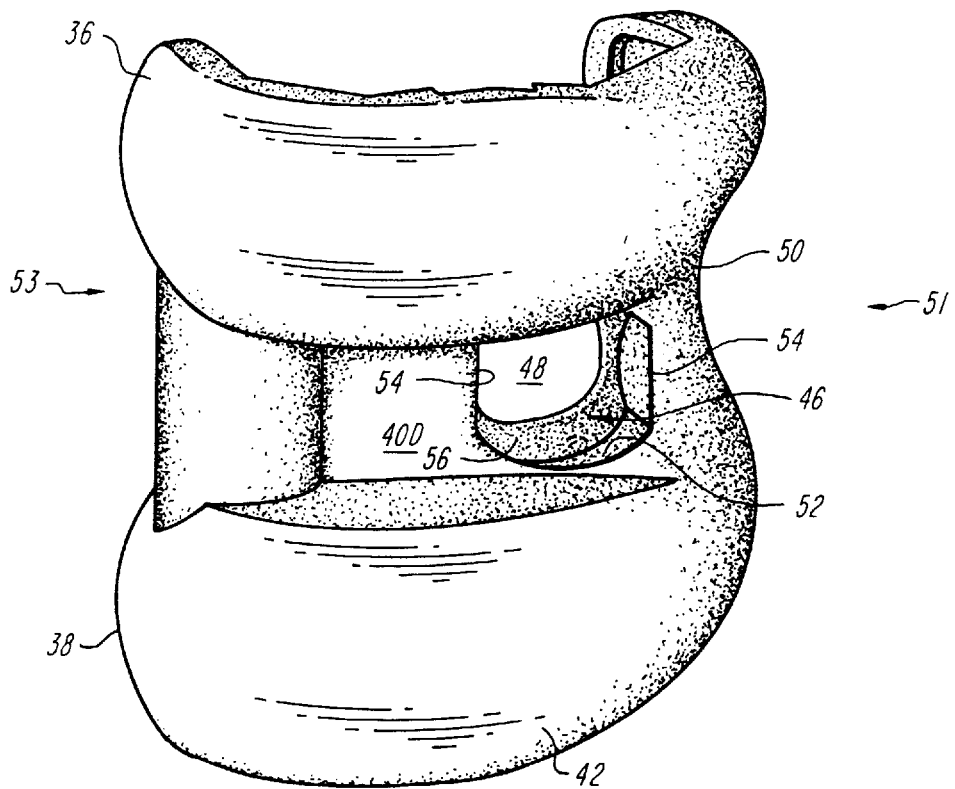
FIG. 3 is a bottom perspective view of the femoral component of FIG. 2.

Referring to FIGS. 1 through 3, the femoral component 16 has a pair of condylar portions 36, 38 that are connected by an intercondylar region or boss 40. The femoral component 16 has a superior articulation surface 42 and an opposed inferior surface 44. Further, the femoral component 16 has a posterior side 53 and an anterior side 51. The anterior side 51 of the femoral component 16 includes a patellar groove 50, shown in FIG. 3, within which seats a patellar prosthetic component (not shown). The superior surfaces 42 of the curved condylar portions 36, 38 articulate with a prosthetic tibial component (not shown) mounted on the head of the tibia, in a manner well known to those of ordinary skill in the art.

The boss structure 40 has a pair of substantially vertical side walls 40A that are generally orthogonal to a top, inferior surface 40B. The top surface 40B preferably has formed thereon a pair of raised ridges 40C that constitute a collar anti-rotation element, as described in further detail below.

With reference to FIGS. 1 and 3, the boss 40 has a cavity 46 formed within a bottom superior surface 40D. An aperture 48 defined by the cavity 46 extends between the superior and inferior surfaces 42, 44, respectively, of the boss structure 40 and has a selected shape such that it can be elongated either in the anterior-posterior direction or the medial-lateral direction. The shape of the aperture can be elliptical, oval, spherical, or of any other suitable shape that allows a sufficient amount of translation of the securing bolt shaft when the bolt is mounted within the aperture.

In the illustrated embodiment, the cavity 46 has a pair of arcuate medial and lateral side walls 52, and a pair of substantially flat anterior and posterior side walls 54 that form a bolt anti-rotation mechanism, as described in further detail below. The cavity 46 further includes an end wall 56 that has a substantially spherical or rounded shape for seating a correspondingly shaped head of the securing bolt 18.

The inferior surface 44 of the condylar portions 36, 38 forms a series of integral surfaces that extend between the anterior and posterior sides of the femoral component. Referring to FIG. 2, the inferior surface of each condylar portion comprises a substantially vertical anterior surface 58, an anterior chamfer surface 60, a substantially horizontal surface 62, a posterior surface 64, and a substantially vertical posterior surface 66. The surface 62 of each condylar portion has an indentation 68 that extends partly into the inferior surface of each condylar portion. The indentation allows the surgeon to grasp and handle the femoral component via a suitable handling instrument. Those of ordinary skill in the art will recognize that the femoral component 16, boss 40, and condylar portions 36,38 can have a variety of shapes.

Figure 4A:
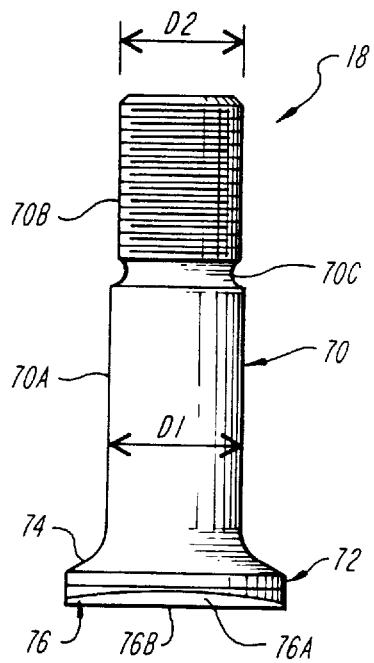
FIG. 4A is a side view of one embodiment of a securing bolt useful with the modular knee prosthesis of FIG. 1.

FIGS. 4A–5B illustrate preferred embodiments of the securing bolt 18 of FIG. 1. With reference to FIG. 4A, the bolt 18 of a first embodiment has a shaft portion 70 that extends upwardly and outwardly from a bolt head 72. The shaft has a lower unthreaded portion 70A that has an outer diameter (D1) less than the outer diameter of bolt head 72, and an upper, threaded portion 70B that is integral with the lower unthreaded portion 70A. An indented neck portion 70C may separate the upper and lower portions 70B, 70A of bolt 18. The outer diameter (D2) of the upper portion 70B can be slightly less than the outer diameter (D1) of the lower shaft portion 70A.

The bolt head portion 72 has a boss aperture-engaging surface 74, and an opposed, top surface 76 that includes a pair of canted surfaces 76A that join at an apex 76B. The aperture-engaging surface 74 can have a rounded or spherical shape complementary to that of the end wall 56 of the boss cavity 46. The mating engagement of the aperture-engaging surface 74 of the bolt head 72 and the shaped end wall 56 of the boss cavity 46 positions the bolt shaft within the aperture 48. The bolt shaft 70 extends from the boss top surface 40B at a selected angle determined by the shape of the aperture 48 and by the mounting angle of the collar 14. The shape of the aperture 48 helps determine the allowable angle and translational range of the bolt shaft by allowing the bolt shaft to angulate and translate within the confines of the aperture, and to eventually seat at a selected position therein, as described in further detail below. Although the end wall 56 and aperture-engaging surface 74 are shown with spherically-shaped contours, those of ordinary skill will recognize that other compatible configurations are possible.

Figure 4B:
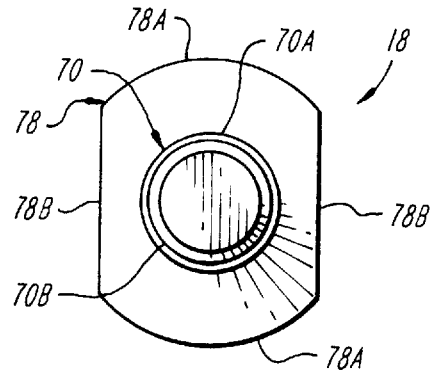
FIG. 4B is a top view of the securing bolt of FIG. 4A.

As illustrated in FIG. 4B, the top surface 76 of the bolt head 72 has a peripheral surface 78 that is defined by a pair of opposed, arcuate sides 78A and a pair of opposed, substantially flat sides 78B. The flat sides 78B matingly engage the flat side walls 54 of the boss cavity 46 and cooperate therewith to secure the bolt within the cavity and to prevent unwanted rotation of the bolt when secured therein.

With further reference to FIG. 4B, in one embodiment the bolt is constructed such that the shaft portion 70 of the bolt extends from a generally centrally located position on the bolt head 72. This arrangement allows the bolt shaft to extend from the inferior surface of the femoral component when the bolt is mounted within the boss aperture at a selected location and desired angle relative to the inferior surface 40B.

Figure 5A:
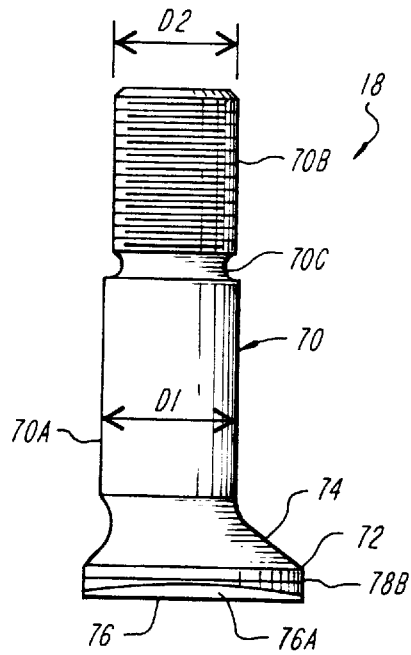
FIG. 5A is a side view of an alternate embodiment of a securing bolt useful with the modular knee prosthesis of FIG. 1.
Figure 5B:
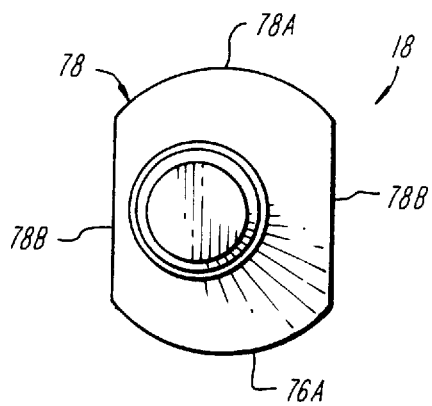
FIG. 5B is a top view, from the shaft, of the securing bolt of FIG. 5A.

FIGS. 5A and 5B illustrate another embodiment of a securing bolt 18 constructed according to the invention. In this embodiment, bolt 18 is similar to that described above and shown in FIGS. 4A and 4B, except that the shaft 70 is positioned on the bolt head 72 in an offset, non-centered position. As illustrated, the shaft portion 70 of the bolt extends upwardly from a position axially offset a selected distance from a generally centrally located position of the bolt head 72. In an exemplary embodiment, the shaft is offset from this generally centrally located position is in the range of about 0 mm to about 5 mm. Preferably, the offset distance is about 2 mm.

This offset construction of the bolt 18 allows the bolt shaft 70 to extend from the boss inferior surface 40B, when the bolt is mounted within the boss aperture, offset from a central or neutral position in either an anterior or a posterior direction, in addition to being oriented at a selected angle and axial orientation relative to the inferior surface 40B of the femoral component 16. For example, an offset bolt (FIGS. 5A and 5B) oriented in either an anterior or posterior direction may be necessary for differing anatomies, or where bony deficiencies exist in certain areas of the femur. By contrast, the illustrated bolt of FIGS. 4A and 4B can be used in both left or right side prostheses where no bolt offset is desired. Thus, the bolts illustrated in FIGS. 4A, 4B, 5A and 5B can be used in both right and left side prostheses where an anterior or posterior, or medial or lateral offset is needed.

Figure 6A:
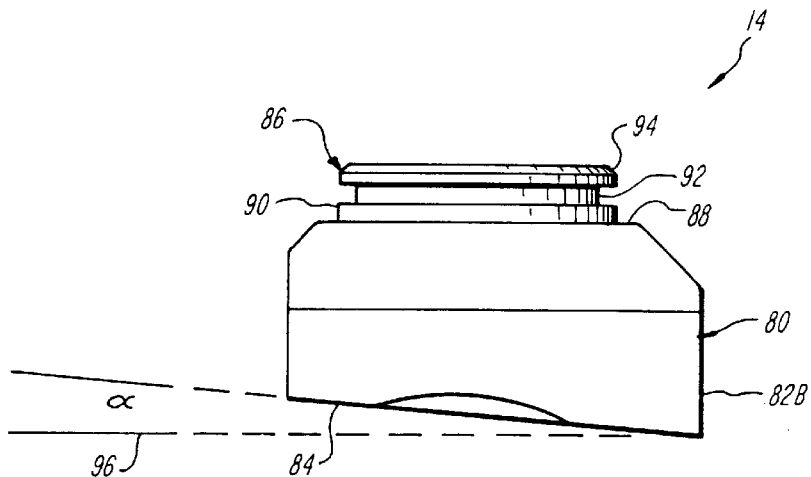
FIG. 6A is a side view of a collar useful with the modular knee prosthesis of FIG. 1.
Figure 6B:
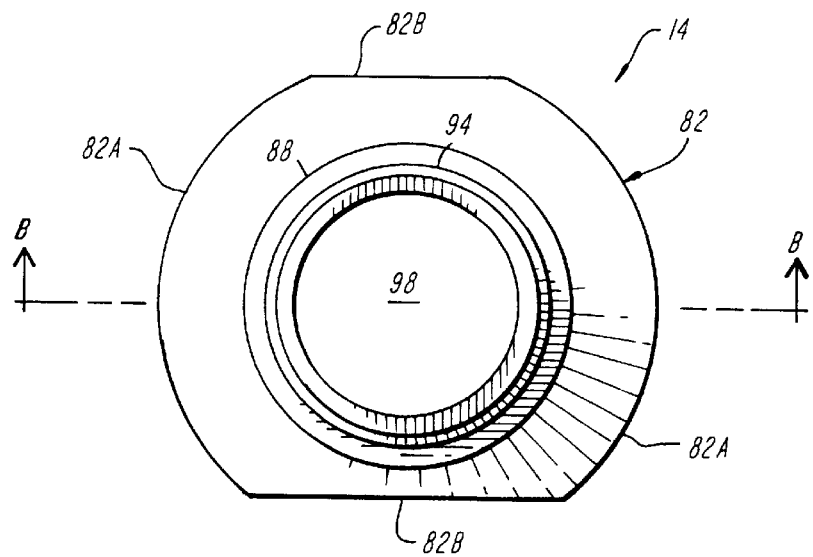
FIG. 6B is a top view of the collar of FIG. 6A.

With reference to FIGS. 6A and 6B, the collar 14 has a central body portion 80 that has an outer peripheral surface 82 and a boss engaging surface 84. The collar 14 can further include a neck portion 86 that extends upwardly from a seating surface 88 if required to mate with a particular Morse taper post configuration. The neck 86 can include a first annular portion 90 and a stepped annular portion 92. A lip 94 formed along the top of the stepped annular surface 92 overhangs the first annular portion 90. The proximal end of the Morse taper post 12, when assembled with the collar 14, engages the seating surface 88.

The boss engaging surface 84 can be canted to form an angle with a transverse plane 96. The transverse plane is defined as the horizontal plane that extends through the knee of an upright subject and that is orthogonal to both the coronal plane and the sagittal plane, as will be appreciated by those having ordinary skill in the art. The engaging surface 84 and the top, inferior surface 40B of the boss 40, which lies in the transverse plane, form a mounting angle "α" when the collar is assembled with the femoral component and engages the boss top surface. The angle "α" is preferably between about 0° and about 15°. According to one practice of the invention, the boss engaging surface 84 can be canted in the anterior-posterior direction to either the anterior or posterior side as measured in the sagittal plane. Likewise, the surface 84 can be canted in the medial-lateral direction to either the medial side or the posterior side as measured in the coronal plane. Preferably, the angle "α" can range between about 0° and about 15° in any direction. This varied collar angulation provides a plurality of mounting angles for the Morse taper post 12 that is compatible with the various possible orientations of the femoral stem when mounted within the distal portion of the femur. Those of ordinary skill in the art will readily appreciate that the boss mounting surface 84 can be configured to provide any combination of coronal and sagittal plane angulations that are constrained by the foregoing angle ranges.

The collar 14 can be used with either right or left side knee prostheses. Generally, the collar is positioned such that the angle is to the lateral side of the prosthesis, as measured in the coronal plane. The same collar can be used in either a left or right side prosthesis by simply reversing the orientation of the collar on the prosthesis to ensure a lateral angle for the Morse taper post 12.

With reference to FIG. 6B, the collar peripheral surface 82 has a pair of opposed arcuate sides 82A and a pair of opposed, flat sides 82B. Flat sides 82B are adapted to engage the raised ridges 40C of the boss top surface 40B. The mating contact between the raised ridges 40C and the flat sides 82B of the collar peripheral surface prevents unwanted rotation of the collar when it is mounted on the boss top surface 40B.

Figure 6C:
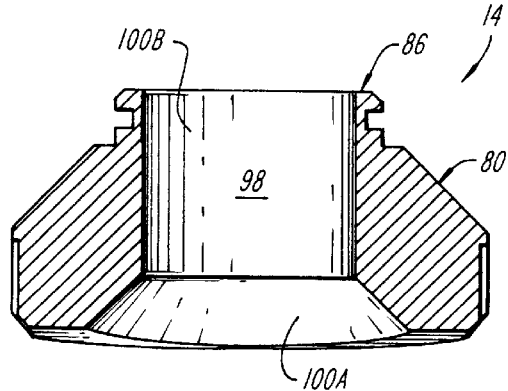
FIG. 6C is a cross-sectional view of the collar of FIG. 6A taken along line B—B of FIG. 6B.

As illustrated in FIG. 6C, the collar 14 further has a central aperture 98 that seats and orients the bolt shaft 70. The aperture 98 has a funnel-like portion 100A adjacent the boss mounting surface 84, and a cylindrical portion 100B that extends from the funnel-like portion 100A to the neck 86 of the collar. The funnel-like portion 100A provides an additional clearance space for bolt insertion.

An exemplary modular knee prosthesis can be assembled in the following manner. The collar 14 is mounted on the top surface 40B, e.g., inferior surface, of the boss 40, and the flat sides 82B of the collar are aligned with the raised ridges 40C. The securing bolt 18 is then inserted into the boss cavity 46 from the underside of the boss and through the boss aperture 48, such that the bolt shaft extends upwardly from the boss inferior surface 40B. The spherical engaging surface 74 of the bolt head 72 mates with and engages the similarly configured end wall 56 of the cavity. The selected shape of the cavity end wall allows the bolt shaft to seat within the cavity at an angle that is determined by the collar 14. The boss mounting surface 84 of the collar 14 determines the angle at which the bolt shaft protrudes into and extends from the collar 14. The threaded portion 70B of the bolt shaft 70 threadedly a threaded portion of the Morse taper post to bind the Morse taper post and collar to the femoral component. In this axially successive assemblage, the collar is pressure fitted between the Morse taper post and boss by the threaded engagement of the bolt and stem.

A significant feature of the present invention is the complementary shape of the cavity end wall and the mounting surface of the securing bolt head, which cooperate to position the securing bolt at a selected angle determined by the collar mounting angle. The varied positions in which the securing bolt shaft can be oriented are facilitated by the selected shape of the aperture. In the modular knee prosthesis of the present invention, the shaft of the securing bolt can be centrally located or offset, depending upon the surgeon's judgment. Additionally, since the collar is pressure fitted between the Morse taper post and boss, the Morse taper post and collar can be separately provided in a packaged modular knee prosthesis. For example, the packaged modular knee prosthesis can include a femoral component, an offset and/or a non offset type securing bolt, a collar or collars having a 5 degree and/or a 7 degree canted mounting surface, and a Morse taper post. The packaged modular knee prosthesis 10 of the invention can further include a femoral sleeve and one or more femoral stems.

Although the securing bolt, collar, and Morse taper post have been illustrated in co-axial configurations, such configurations are not required by the invention. For example, depending on the dimensions of the securing bolt, collar and Morse taper post, the securing bolt can project through the aperture in the femoral component and the collar so as to be perpendicular to the inferior surface; however, the boss mounting surface or the neck of the collar can be canted to angle the Morse taper post as desired.

Referring now to FIG. 7, a modular knee prosthesis 102 is illustrated that does not include a femoral sleeve. In this embodiment, a femoral stem 104 is adapted for mating directly with a Morse taper post 106. More particularly, the femoral stem includes a first end 108 that defines a cavity 110 that is tapered to provide a friction fit over the Morse taper post 106. A second end 112 of the femoral stem is adapted for placement in a patient's medullary canal. In substantially all other respects, however, the remaining components of the modular knee prosthesis are identical to the components illustrated in FIG. 1.

With respect to each of the preceding embodiments, a modular collar 14 increases the adaptability of the modular knee prosthesis 10. However, other embodiments of the invention include a Morse taper post that has features of the collar, such as a canted boss mounting surface, funnel-like portion, opposed arcuate sides, and opposed flat sides. As these configurations could preclude the Morse taper post from rotating during assembly, because its base is lodged between the raised ridges of the femoral component, a securing bolt can be provided that is rotatable with respect to the femoral component to urge the securing bolt and Morse taper post together.

Figure 8:
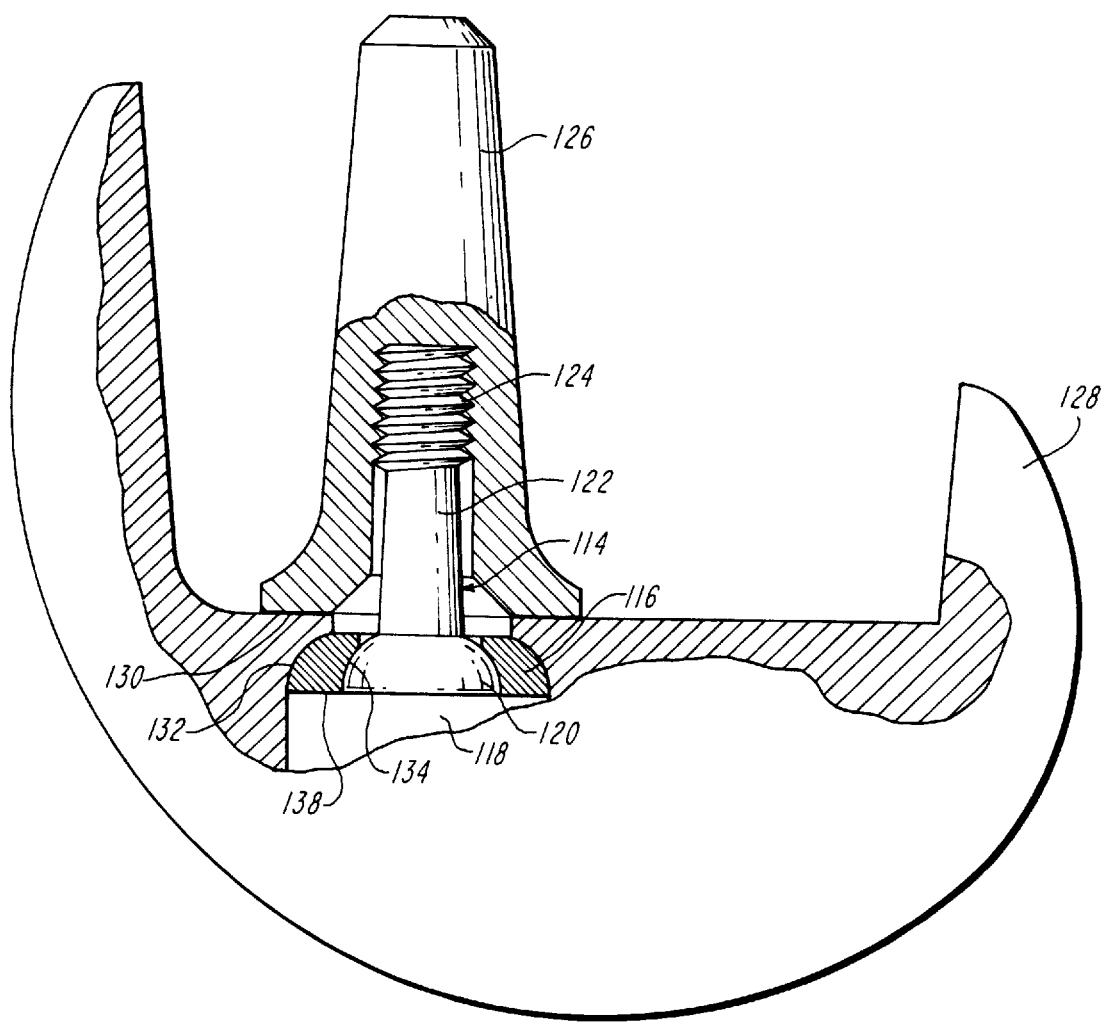
FIG. 8 is a cutaway view of an alternative embodiment of the invention having a bolt and washer fastening system and that does not include a collar.
Figure 9:
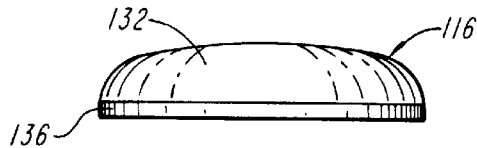
FIG. 9 is a side view of a washer in accordance with the invention.

For example, FIG. 8 is a cutaway view of an alternative embodiment of the invention having a securing bolt and washer fastening system that does not include a collar, for use with a femoral component. In this embodiment, the securing bolt of FIGS. 1–6 is replaced by a bolt 114 and a washer 116, wherein the bolt and washer are rotatable with respect to each other and are collectively cooperative with the configuration of a boss cavity 118 to facilitate angulation and translation of the bolt as described above with respect to FIGS. 1–7. The bolt includes a head 120, a shank 122, and an engagement feature 124 such as threads. A supplemental component 126, such as a Morse taper post or femoral stem includes features, such as threads, that cooperate with the engagement feature 124 of the bolt 114 to allow the bolt to be firmly mated to the supplemental component and a femoral component 128. As a Morse taper post is illustrated in FIG. 8, the supplemental component 126 will be referred to as such during the descriptions that follow.

The lateral angulation of the Morse taper post 126 with respect to the femoral component 128 is determined by the cant of a boss mounting surface 130. In FIG. 8, the plane defined by the boss mounting surface 130 is substantially perpendicular to the longitudinal axis of the Morse taper post to provide a neutral or 0 degree orientation. In other embodiments, the boss mounting surface defines a plane that is not perpendicular to the longitudinal axis of the Morse taper post to provide a selected angulation to the right or left with respect to the front of the femoral component.

Positioning or translation of the bolt 114 fore and aft is accomplished by selection of an appropriate washer 116 as illustrated in FIGS. 9–16. Each of the illustrated washers 116 includes a spherical boss-engaging or inferior surface 132, a contoured bolt head-engaging or superior surface 134, a peripheral surface 136, a top surface 138, a pair of opposed, arcuate sides 140, and a pair of opposed substantially flat sides 142. The flat sides 142 matingly engage a flat side wall of the boss cavity 118 and cooperate therewith to secure the washer 116 within the cavity and prevent unwanted rotation of the washer in a manner similar to that described above with respect to FIG. 4B.

Figure 10:
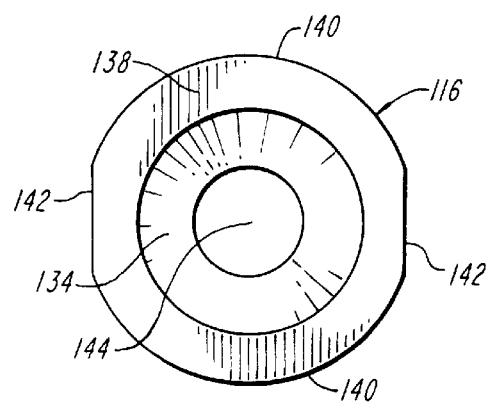
FIG. 10 is a top view of a washer in accordance with the invention.
Figure 11:
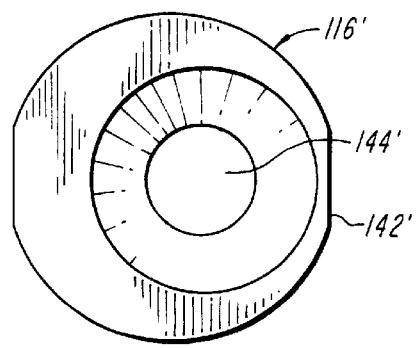
FIG. 11 is a top view of an alternative embodiment of a washer in accordance with the invention.

Referring now to FIG. 10, a top view of a washer 116 in accordance with the invention is illustrated, wherein an aperture 144 is in the center of the washer. A washer having this configuration is selected when no offset of the bolt 114 is required. By contrast, FIG. 11 illustrates a washer 116' wherein an aperture 144' is not at center of the washer, but is offset toward one of the substantially flat sides 142'. Thus, offset of the bolt 114 can be achieved with this washer by orienting the washer within the boss cavity 118 so that the aperture 144' is either closer to the front or the back of the femoral component 128.

Figure 12:
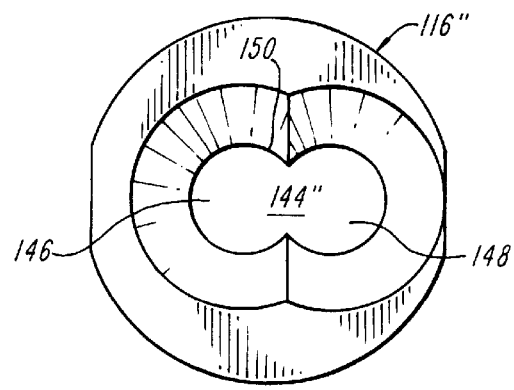
FIG. 12 is a top view of an yet another embodiment of a washer in accordance with the invention.
Figure 13:
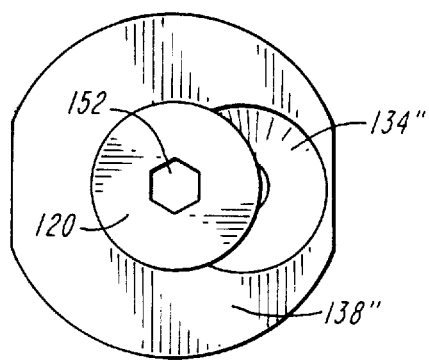
FIG. 13 is an end view of the washer of FIG. 12 in association with a bolt in a first position.
Figure 15:
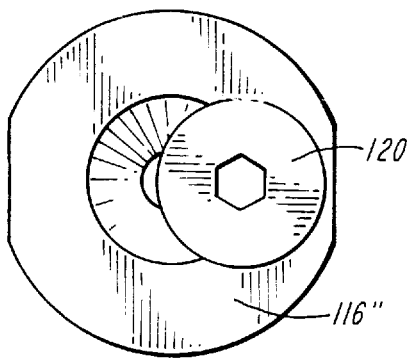
FIG. 15 is an end view of the washer of FIG. 12 in association with a bolt in a second position.

FIG. 12 illustrates an embodiment of the washer 116" having a double-lobed aperture 144", wherein each of the aperture lobes 146 and 148 is dimensioned to receive the bolt shank 122 therethrough. A neck portion 150 locally reduces the diameter of the aperture 144" and defines the first and second lobes 146, 148. At the neck portion 150, the aperture 144" has a smaller diameter than the bolt shank 122. However, the open configuration of the neck portion 150 allows a curved side portion of the bolt head or shank to extend into the principally unoccupied lobe as shown in FIGS. 13 and 15. This double-lobed configuration provides particular benefits in an application requiring a bolt to be positioned in either of a first or a second precisely defined location, but wherein the required bolt shank or head dimensions in association with the close proximity of the first location to the second location preclude the provision of two separate and distinct apertures. Additionally, a double-lobed configuration having a first lobe centrally located and an offset second lobe allows a single washer to be used in a kit to provide fore, neutral, and aft positioning of the bolt 120 by appropriate orientation of the washer within the femoral component and insertion of the bolt through on of the lobes.

Figure 14:
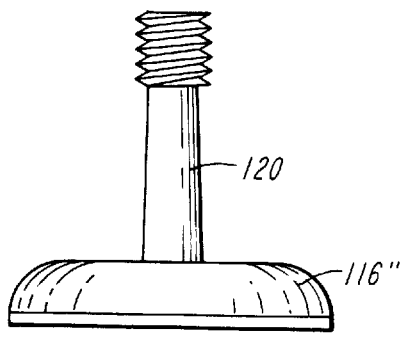
FIG. 14 is a side view of the bolt and washer of FIG. 13.
Figure 16:
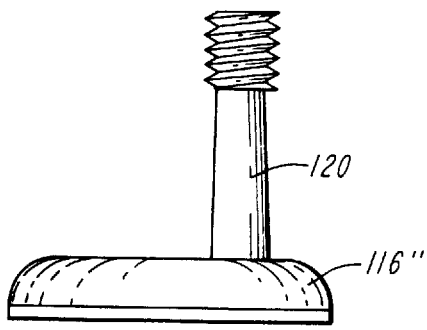
FIG. 16 is a side view of the bolt and washer of FIG. 15.

FIG. 13 is an end view of the washer 116" of FIG. 12 in association with a bolt in a first, central position and FIG. 14 is a side view of the bolt and washer of FIG. 13. The bolt 120 is illustrated with a slot 152 having six flattened sides suitable for engaging a hex wrench; however, the bolt head can be provided with other configurations known to those skilled in the art to permit the bolt to be tightened with a tool or by hand. FIG. 15 is an end view of the washer of FIG. 12 in association with a bolt in a second, offset position and FIG. 16 is a side view of the bolt and washer of FIG. 14.

Thus, an exemplary kit may include a selection of washers, a single bolt, and a selection of Morse taper posts and/or femoral stems, and be assembled in the following manner. A Morse taper post having the desired angulation is selected and mounted on the top surface of the boss, and the flat sides of the Morse taper post are aligned between the raised ridges. A washer having the desired aperture location is selected and a bolt is inserted through the aperture. The washer is then inserted into the boss cavity from the underside of the boss and the bolt shank is passed through the boss aperture, such that the bolt shaft extends upwardly from the boss inferior surface. The spherical engaging surface of the washer mates with and engages the similarly configured end wall of the cavity and the sides of the washer engage the sides of the boss cavity to inhibit rotation of the washer. The selected shape of the washer and location of the aperture determines the offset of the bolt. The threads of the bolt engage the threads of the Morse taper post and the bolt is rotated to urge the bolt and Morse taper post together.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

What is claimed is:

1. A medical fastening system for a modular knee prosthesis comprising:

a femoral component having a superior surface, an inferior surface, and an aperture extending therebetween;

a bolt including a head portion engagable with the superior surface of the femoral component to inhibit movement of the bolt through the aperture in the femoral component, and an elongate shaft portion extending from the head portion of the bolt, the elongate shaft portion having a length sufficient to protrude through the aperture in the femoral component beyond the inferior surface of the femoral component; and a supplemental component having an outer surface for engaging an elongate prosthetic component, the supplemental component being engagable with the elongate shaft portion of the bolt to place an end portion of the supplemental component in contact with the inferior surface of the femoral component, wherein the supplemental component is a Morse taper post, and wherein the supplemental component includes a longitudinal axis, a base defining an aperture therein for receiving the elongate portion of the bolt therein and defining a plane that is angled less than 90 degrees with respect to the longitudinal axis.

2. A medical fastening system for a modular knee prosthesis comprising:

a femoral component having a superior surface, an inferior surface, and an aperture extending therebetween;

a washer having a superior surface, an inferior surface, and an aperture extending therebetween, the inferior surface of the washer being engagable with the superior surface of the femoral component to inhibit movement of the washer through the aperture in the femoral component; and a bolt including a head portion engagable with the superior surface of the washer to inhibit movement of the bolt through the aperture in the washer, and an elongate shaft portion extending from the head portion of the bolt, the elongate shaft portion having a length sufficient to protrude through the aperture in the washer and the aperture in the femoral component beyond the inferior surface of the femoral component, wherein the aperture of the washer is smaller than the aperture in the femoral component, the aperture in the washer is not in the center of the washer, the aperture in the femoral component is elongate and has an anterior portion and a posterior portion, wherein the washer is matable with the femoral component in a first orientation to position the aperture of the washer toward the anterior portion of the aperture of the femoral component, and wherein the washer is matable with the femoral component in a second orientation to position the aperture of the washer toward the posterior portion of the aperture of the femoral component.

3. The medical fastening system of claim 2 wherein the washer includes a peripheral region that defines a pair of opposed arcuate portions and a pair of opposed flattened portions, the femoral component includes a boss cavity that defines the aperture of the femoral component, the boss cavity including a pair of opposed arcuate portions and a pair of opposed flattened portions, the washer being insertable into the boss cavity in one of a first orientation and a second orientation, and once inserted being non-rotatable with respect to the femoral component.

4. A medical fastening system for a modular knee prosthesis comprising:

a femoral component having a superior surface, an inferior surface, and an aperture extending therebetween;

a washer having a superior surface, an inferior surface, and an aperture extending therebetween, the inferior surface of the washer being engagable with the superior surface of the femoral component to inhibit movement of the washer through the aperture in the femoral component; and a bolt including a head portion engagable with the superior surface of the washer to inhibit movement of the bolt through the aperture in the washer, and an elongate shaft portion extending from the head portion of the bolt, the elongate shaft portion having a length sufficient to protrude through the aperture in the washer and the aperture in the femoral component beyond the inferior surface of the femoral component, wherein the aperture of the washer includes first and second lobes dimensioned to receive the shank of the bolt therethrough, the first and second lobes being defined by a neck portion of the washer having a diameter less than the diameter of the shank, wherein the aperture in the femoral component has an anterior portion, a central portion, and a posterior portion, and wherein the washer is matable with the femoral component to align the first lobe of the washer with one of the anterior portion and the posterior portion of the aperture of the femoral component, and the second lobe portion with the central portion of the aperture of the femoral component.

5. A medical fastening system for a modular knee prosthesis comprising:

a femoral component having a superior surface, an inferior surface, and a boss cavity that defines an aperture extending between the superior surface and the inferior surface, the boss cavity including a pair of opposed arcuate portions and a pair of opposed flattened portions;

a washer having a superior surface, an inferior surface, and an aperture extending therebetween, the inferior surface of the washer being engagable with the superior surface of the femoral component to inhibit movement of the washer through the aperture in the femoral component, a peripheral region that defines a pair of opposed arcuate portions and a pair of opposed flattened portions, the washer being insertable into the boss cavity in one of a first orientation and a second orientation, and once inserted being non-rotatable with respect to the femoral component;

a bolt including a head portion engagable with the superior surface of the washer to inhibit movement of the bolt through the aperture in the washer, and an elongate shaft portion extending from the head portion of the bolt, the elongate shaft portion having a length sufficient to protrude through the aperture in the washer and the aperture in the femoral component beyond the inferior surface of the femoral component; and a Morse taper post engagable with the elongate shaft portion of the bolt, the Morse taper post including a longitudinal axis, a base defining an aperture therein for receiving the elongate portion of the bolt therein and defining a plane having a selected orientation with respect to the longitudinal axis, and a tapered distal end.

6. The medical fastening system of claim 5, wherein the aperture of the washer includes first and second lobes dimensioned to receive the shank of the bolt therethrough, the first and second lobes being defined by a neck portion of the washer having a diameter less than the diameter of the shank, wherein the aperture in the femoral component has an anterior portion, a central portion, and a posterior portion, and wherein the washer is matable with the femoral component to align the first lobe of the washer with one of the anterior portion and the posterior portion of the aperture of the femoral component, and the second lobe portion with the central portion of the aperture of the femoral component.

* * * * *